United States Patent [19]
Zhang et al.

[11] Patent Number: 6,054,622
[45] Date of Patent: Apr. 25, 2000

[54] AROMATIC HYDROXYTHIOL SYNTHESIS USING DIAZONIUM SALTS

[75] Inventors: Mingbao Zhang, Morris County, N.J.; David Ryckman, Seattle, Wash.; Eric MacMillan, Morris County, N.J.

[73] Assignee: AlliedSignal Inc, Morristown, N.J.

[21] Appl. No.: 09/213,144

[22] Filed: Dec. 18, 1998

[51] Int. Cl.$^7$ .................................................. C07C 319/02
[52] U.S. Cl. .............................. 568/62; 568/61; 548/544; 549/62; 549/476; 549/505
[58] Field of Search .................. 568/61, 62, 67; 548/543, 544; 549/62, 476, 505, 544

[56] References Cited

U.S. PATENT DOCUMENTS

| | | | |
|---|---|---|---|
| 2,286,701 | 6/1942 | Werner | 430/187 |
| 2,820,780 | 1/1958 | Gutcho | 530/336 |
| 3,479,407 | 11/1969 | Laufer | 568/23 |
| 4,734,527 | 3/1988 | Krauss | 568/47 |
| 4,948,827 | 8/1990 | Christidis | 524/392 |

OTHER PUBLICATIONS

Watson et al., *J. Chem. Soc.*, 121, 2414 (1922).
Yiannios et al., *J. Org. Chem.*, 28, 3246 (1963).
Cohen et al., *J. Org. Chem.*, 42(12), (1977).
Allen et al., *Org. Synth. Coll.*, 1, 580 (1943).
Ungnade et al., *Org. Synth. Coll.*, 3, 130 (1955).
J Chem Soc by Watson and Dutt 121 pp. 2414–2419, 1922.
J Amer Chem Soc By Djerassi vol. 77 pp. 568–571, 1955.
Gazz Chim Ital 99 by Cabiddu pp. 1095–1106, 1969.
CA:119:117042 ab of Zh Org Khim by Ganushchak 28(3) pp. 531–6, 1992.

*Primary Examiner*—Gary Geist
*Assistant Examiner*—Jean F Vollano
*Attorney, Agent, or Firm*—Colleen D. Szuch

[57] ABSTRACT

A method for the preparation of aromatic hydroxythiols including oxidizing an aromatic aminothiol to form an aminodisulfide compound; forming a bis-diazonium salt of the aminodisulfide compound; and reacting the bis-diazonium salt with water to form an aromatic hydroxyldisulfide compound, which is then reduced to the hydroxythiol. New bis-diazonium aromatic disulfide compounds are also disclosed.

14 Claims, No Drawings

AROMATIC HYDROXYTHIOL SYNTHESIS USING DIAZONIUM SALTS

FIELD OF THE INVENTION

The present invention relates to the preparation of aromatic hydroxythiol compounds, and, more specifically, to the preparation of isomerically pure hydroxythiophenols. In particular, the present invention relates to a commercially feasible hydroxythiophenol synthesis in which significant quantities of the isomerically pure reaction product are obtained.

DESCRIPTION OF THE PRIOR ART

Diazonium salt reactions are generally employed to substitute an aromatic ring with a hydroxyl group. The diazonium salt reaction of aromatic thiols, however, produces a poor yield of diazonium salt. Furthermore, aromatic thiols are nucleophiles that tend to react violently with diazonium reagents.

Isomerically pure hydroxythiophenols are important reagents and starting materials for a variety of pharmaceutical, agrochemical and chemical processes. 3-Hydroxythiophenol, in particular, has been used as a key starting material for the synthesis of a new drug for the prevention of breast cancer. The commercial demands for these compounds have created a need for their practical large scale production.

An isomerically pure hydroxythiophenol could be prepared by reacting an isomerically pure aminothiophenol with $NaNO_2$ and $H_2SO_4$ to form the corresponding diazonium salt, which could then be converted to a hydroxythiophenol by reaction with water. However, consistent with other aromatic thiol compounds, low yields are obtained. There remains a need for a commercially practical method of producing isomerically pure hydroxythiophenols in high yield.

DETAILED DESCRIPTION OF THE PREFERRED EMBODIMENT

This need is met by the present invention. It has now been discovered that oxidation of aromatic thiols to create a disulfide linkage between two thiol groups eliminates the reactivity of the thiol sulfur toward diazonium reagents. The use of the disulfide structure as an internal self-protecting group eliminates the need for additional reagents for carrying out protection of the thiophenol group. This is particularly advantageous for the production of isomerically pure hydroxythiophenols.

Furthermore, many of the process steps can be performed in one pot, without the intervening extraction and washing steps. Species are not formed by de-protection of the thiophenol that would require removal in an additional washing step.

The present invention thus provides an improved method the preparation of aromatic hydroxythiol compounds in which, as shown in Step I, an aromatic aminothiol compound is oxidized to form an aromatic aminodisulfide:
Step I:

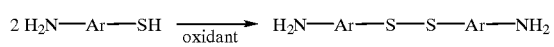

Ar is selected from aryl, aralkyl or heterocyclic rings or a fused ring structure of from two to ten of such rings. The bis-diazonium salt of the aromatic aminodisulfide is then formed, as shown in Step II, by treating the aromatic aminodisulfide with $NaNO_2$ and $H_2SO_4$:
Step II:

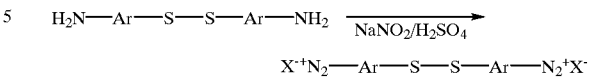

The bis-diazonium salt is then reacted with water, as shown in Step III, to form an aromatic hydroxyldisulfide compound:
Step III:

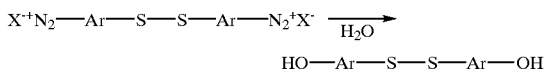

The disulfide bond is then reduced, as shown in Step IV, to obtain the aromatic hydroxythiol compound:
Step IV:

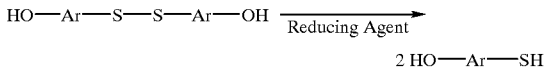

Because the reaction itself does not generate isomers, the method of the present invention is useful for the synthesis of isomerically pure aromatic hydroxythiol compounds, and particularly useful for the synthesis of isomerically pure hydroxythiophenol compounds. Hydroxythiophenol synthesis is depicted in Steps I–IV when Ar is an unsubstituted or substituted phenyl group.

For purposes of the present invention, an "isomerically pure" reaction product contains the same level of isomeric impurities as its starting material. Therefore, with the method of the present invention, the isomeric purity of the reaction product will depend upon the isomeric purity of its starting material, and it is possible to obtain an isomeric purity of 95 wt % and greater. Thus, to obtain an isomerically pure end product, an isomerically pure starting material must be employed.

Another aspect of the present invention provides bis-diazonium salt compounds having the structure depicted in Formula I:

(I)

Both Ar groups are the same and are selected from divalent substituted or unsubstituted aromatic radicals, divalent substituted or unsubstituted araliphatic radicals, divalent substituted or unsubstituted heterocyclic radicals and fused ring structures formed therefrom containing from two to ten rings.

The method of the present invention utilizes aromatic aminothiol compounds as starting materials. The compounds are commercially available. Alternately, they may be prepared using essentially conventional techniques. Aromatic aminothiol starting materials suitable for use with the present invention have the structure of Formula II:

(II)

Ar is as described above for Formula I. More preferably, Ar is a substituted or unsubstituted $C_6$–$C_{15}$ aryl radical, a substituted or unsubstituted $C_7$–$C_{13}$ aralkyl radical, a substituted or unsubstituted 3–6 member heterocyclic radical, or a two or three ring fused ring structure of any of the foregoing. Essentially any substitution groups that are inert toward diazonium salt-forming reagents or are capable of being protected from reaction with diazonium salt-forming reagents may be employed. Suitable substitution groups, substitution groups requiring protecting groups, protecting groups and methods of protection are well-known. Examples of substitution groups include $C_1$–$C_6$ aliphatics such as alkyls, alkoxys and alkenyls, $C_6$–$C_{15}$ aryls, $C_3$–$C_8$ cyclic aliphatics, amidos and secondary and tertiary aminos.

Ar as a 3–6 ring member heterocyclic radical may include known heterocyclic atoms such as N, O and S. Suitable heterocycles include, for example, pyran, thiophene, pyrrole, furan, pyridine, or derivatives thereof. Ar as a $C_6$–$C_{15}$ aryl may be, for example, phenyl, o-tolyl, m-tolyl, p-tolyl, o-xylyl, m-xylyl, p-xylyl, alpha-naphthyl or beta-naphthyl. Ar as a $C_7$–$C_{20}$ aralkyl radical may be, for example, benzyl, 4-methylbenzyl, o-methylbenzyl, p-methylbenzyl, diphenylmethyl, 2-phenylethyl, 2-phenylpropyl or 3-phenylpropyl, and preferably a $C_7$–$C_9$ aralkyl, especially benzyl. Any of these groups may be substituted, for example, with substituted or unsubstituted, straight-chained or branched $C_1$–$C_{20}$ alkyl, aryl, aralkyl, amido, alkoxyl and secondary and tertiary amino groups.

In a preferred embodiment, Ar is $C_6$–$C_{14}$ aryl, especially phenyl or naphthyl. When the aryl or aralkyl group of Ar is a phenyl or alkylphenyl group the compound of Formula II is a starting material for hydroxythiophenols having the structure of Formula III:

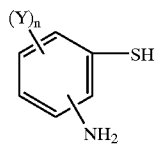

(III)

Y is selected from straight-chained or branched, unsubstituted or substituted $C_1$–$C_{20}$ alkyl, aryl, aralkyl, amido, alkoxyl and secondary and tertiary amino groups; and n is between 0 and 4, inclusive.

The aromatic aminothiol starting materials can be obtained commercially, or, as shown below, by reducing corresponding aromatic nitrosulfonyl chlorides:

Scheme I:

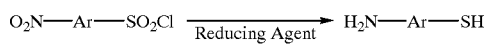

Essentially any well-known reagent capable of reducing an aromatic nitrosulfonyl chloride to an aromatic thiophenol can be used. Suitable reagents, solvents and process conditions may be determined by reference to March, J., *Advanced Organic Chemistry* (2nd Ed., McGraw-Hill, 1977), (the disclosure of which is incorporated herein by reference) and through routine optimization of reaction parameters. Examples of suitable reducing agents include hydroiodic acid, metal/concentrated mineral acid combinations such as Zn, Sn or Fe and concentrated hydrochloric or sulfuric acid, or hydrides such as $NaBH_4$ or $LiAlH_4$.

The aromatic aminothiol starting materials can also be made, as shown in Scheme II, by reducing aromatic aminosulfonic acids and derivatives thereof after the amine function has been suitably protected:

Scheme II:

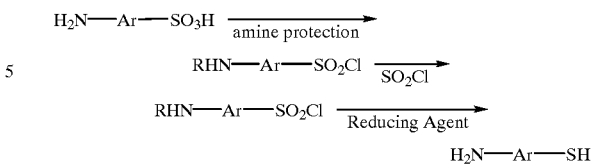

Suitable reagents, solvents, protecting groups, protection reactions and process conditions may be determined by reference to the above-cited *Advanced Organic Chemistry*, and through routine optimization of reaction parameters. $PCl_5$ can be used instead of $SO_2Cl$. The reducing agents used in Scheme I can also be used in Scheme II.

Accordingly, isomerically pure end products may be obtained by starting with isomerically pure aromatic nitrosulfonyl chlorides, which are also commercially available or may be prepared by known methods. Isomerically pure aromatic nitrosulfonyl chlorides, when not available commercially, are prepared using well-known nitration and sulfonation reactions. Suitable reagents, solvents and process conditions may by determined by reference to the above-cited *Advanced Organic Chemistry* and through routine optimization of reaction parameters. The aromatic nitrosulfonyl chlorides that form have distinct boiling points and are separated on a commercial scale by distillation.

The aromatic aminothiol compound is then allowed to undergo oxidation in the Step I to form a disulfide dimer. Essentially any oxidizer capable of forming a sulfur bridge between two thiol groups may be used. This reaction step is essentially conventional, and suitable reagents, solvents and process conditions may be determined by reference to Yiannios et al., *J. Org. Chem.*, 28, 3246(1963), the disclosure of which is incorporated herein by reference.

For Example, the oxidation may be performed by heating the aromatic aminothiol with an oxidant such as DMSO or 30% aqueous hydrogen peroxide at a temperature between about 50 and about 150° C., and preferably between about 80–90° C., to form disulfide linkages between the thiol groups, thereby converting the aminothiol compound to an amino disulfide compound having the structure of Formula IV:

 (IV)

The Ar groups are identical, and are as described above for Formula I. One of ordinary skill in the art will understand that with oxidants such as hydrogen peroxide that tend to decompose at elevated temperatures, lower temperatures within the 50 to 150° C. range should be employed.

When Ar is a phenyl or alkylphenyl group, the compound is an intermediate in the preparation of hydroxythiophenols having the structure of Formula V:

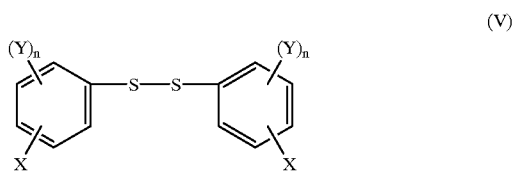

(V)

Y and n are as described above with respect to Formula III and X is an amino group.

The reaction mixture is washed with cold water and then extracted into an organic solvent. Essentially any organic solvent in which an aromatic disulfide is soluble may be employed. Examples include ethers such as MTBE, diethyl ether or isopropyl ether, ethyl acetate or halogenated solvents such as dichloromethane or chloroform. The organic phase is then washed with water and purified by vacuum distillation. These steps are also essentially conventional, and suitable reagents, solvents and process conditions may be determined by reference to the above-cited publication by Yiannios et al. in *J. Org. Chem.*

The amino disulfide compound is then allowed to undergo the diazonium salt-forming reaction of Step II. This reaction step is also essentially conventional, and suitable reagents, solvents and process conditions may be determined by reference to Cohen et al., *J. Org. Chem.*, 42, 2053 (1977), the disclosure of which is incorporated herein by reference. For example, the known reaction with $NaNO_2$ and $H_2SO_4$ disclosed in this publication may be employed.

In this reaction, the aromatic aminodisulfide is dissolved in an aqueous sulfuric acid solution, which is then cooled to a temperature between about 5 and about 40° C. Sodium nitrite is slowly added while maintaining the temperature within the foregoing range. One of ordinary skill in the art will understand that higher reaction temperatures can be employed with slower rates of addition. After the addition is completed, urea is added to consume any excess sodium nitrite, optionally followed by the addition of water. A solution is obtained of a bis-diazonium salt having the structure of Formula VI:

$$X^{-+}N_2-Ar-S-S-Ar-N_2^+X^-$$ (VI)

X is a counter-ion and Ar is as described above for Formula I. When Ar is a phenyl or alkylphenyl group, the compound is an intermediate in the preparation of hydroxythiophenols having the structure of Formula VII:

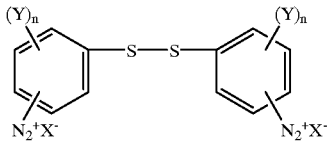

(VII)

Y and n are as described above for Formula III, and X is a counter-ion. Examples of typical counter-ions that form include sulfate and hydrosulfate.

The bis-diazonium salt solution is kept cold prior to the replacement of the diazonium salt groups with hydroxy groups. The cold solution is then added in small portions to an aqueous sulfuric acid solution heated to between about 80 and about 150° C., and preferably to about 110° C., at which the reaction mixture is maintained for between about 30 minutes and about two hours. A conventional catalyst at room temperature may alternatively be employed. This reaction step is also essentially conventional, and suitable reagents, solvents and process conditions may be determined by reference to the above-cited publication by Cohen et al. in *J. Org. Chem.*

The reaction mixture is then cooled to yield an aromatic hydroxyldisulfide having the structure of Formula VIII:

$$HO-Ar-S-S-Ar-OH$$ (VIII)

Ar is as described above for Formula I. When Ar is a phenyl or alkylphenyl group, the compound is an intermediate in the preparation of hydroxythiophenols having the structure of Formula V in which each X is a hydroxyl group and Y and n are as described above for Formula III. The reaction mixture is then extracted as in Step I with an organic solvent such as an ether, acetate or halogenated hydrocarbon. The organic layer is then concentrated by the well-known technique of evaporation, optionally with reduced pressure, to afford the crude disulfide.

The disulfide linkage is then reduced to liberate the isomerically pure aromatic hydroxythiol. Essentially any agent capable of reducing a disulfide linkage may be used. For example, the disulfide linkage may be reduced by treatment with a reducing agent such as a mixture of sodium metabisulfite and KOH, or a mixture of a metal (such as Zn, Fe or Sn) and $H^+$. Reducing agents such as sodium metabisulfite or metal hydrides such as sodium borohydride or lithium aluminum hydride may also be employed. Suitable reagents, solvents and process conditions my be determined by reference to the above-cited *Advanced Organic Chemistry* and through routine optimization of reaction parameters.

The precipitated aromatic hydroxythiols are then isolated from the reaction mixture by extraction as in Step I, with an organic solvent such as an ether, acetate or halogenated hydrocarbon. The resulting aromatic hydroxythiol has the structure of Formula IX:

$$HO-Ar-SH$$ (IX)

Ar is as described above for Formula I. When Ar is a phenyl or alkylphenyl group, the compound is a hydroxythiophenols having the structure of Formula V in which each X is a hydroxyl group and Y and n are as described above for Formula III.

EXAMPLES

Unless disclosed to be otherwise, reactions are performed at room temperature or at ambient pressure.

Example 1

Preparation of 3-Hydroxythiophenol

3-Aminothiophenol (5 g, 40 mmol) was oxidized to 3-aminophenyl disulfide with one equivalent dimethyl sulfoxide (DMSO) (20 g, 26 mmol) at 80–90° C. in near quantitative yield as shown by GC. Without isolation, the reaction mixture was poured into a dilute sulfuric acid solution (7.2 mL concentrated sulfuric acid in 50 mL water) to obtain a milk-like white suspension which was doubly diazotized using a solution of $NaNO_2$ (2.5 g) in water (8 mL) at room temperature. The diazonium salt solution (orange color) was then thermally decomposed by carefully dripping into a refluxing solution of sulfuric acid (20 mL) and water (10 mL). A dark brown mixture was obtained when the addition was completed. The reaction was monitored by GC by extracting an aliquot into isopropyl ether, which showed a near clean formation of the desired disulfide. The reaction mixture was then cooled in an ice-water bath followed by rapid addition of Zn dust. The reaction was gradually warmed to room temperature and heated at reflux. The dark brown color faded away and the reaction mixture became off-white. The reaction was monitored by GC by extracting an aliquot into isopropyl ether. The product 3-hydroxythiophenol was isolated by isopropyl ether extraction in 73% yield from 3-aminothiophenol. Both GC and $^1H$ NMR showed good purity.

Example 2

Preparation of 2-Hydroxythiophenol

2-Hydroxythiophenol is prepared according to the method of Example 1, using as the starting material 2-aminophenol.

Example 3

Preparation of 2-Thio-4-Hydroxytoluene

2-Thio-4-hydroxytoluene is prepared according to the method of Example 1, using as the starting material 2-thio-4-aminotoluene.

Example 4

Preparation of 2-Thio-5-Hydroxy-p-Xylene

2-Thio-5-hydroxy-p-xylene is prepared according to the method of Example 1, using as the starting material 2-thio-5-amino-p-xylene.

Example 5

Preparation of 1-Thio-4-Hydroxy-Naphthalene

1-Thio-4-hydroxy-naphthalene is prepared according to the method of Example 1, using as the starting material 1-thio-4-amino-naphthalene.

Example 6

Preparation of 2-Thio-3-Hydroxy-Thiophene

2-Thio-3-hydroxy-thiophene is prepared according to the method of Example 1, using as the starting material 2-thio-3-amino-thiophene.

Example 7

Preparation of 2-Thio-4-Hydroxy-Furan

2-Thio-4-hydroxy-furan is prepared according to the method of Example 1, using as the starting material 2-thio-4-amino-furan.

Example 8

Preparation of 2-Thio-3-Hydroxy-Pyrrole

2-Thio-3-hydroxy-pyrrole is prepared according to the method of Example 1, using as the starting material 2-thio-3-amino-pyrrole.

The present invention thus provides a practical, commercially viable method for the preparation of hydroxythiophenols from readily available starting materials.

What is claimed is:

1. A method for the preparation of aromatic hydroxythiols comprising the steps of oxidizing a diazonium salt-forming aromatic aminothiol to form an aminodisulfide compound; forming a bis-diazonium salt of said aminodisulfide compound; and reacting said bis-diazonium salt with water to form an aromatic hydroxyldisulfide compound.

2. The method of claim 1, further comprising the step of reducing the disulfide bond of said disulfide to form an aromatic hydroxythiol.

3. The method of claim 1, wherein said aromatic aminothiol has the structure:

wherein Ar is selected from the group consisting of substituted or unsubstituted aromatic radicals, substituted or unsubstituted araliphatic radicals, substituted or unsubstituted heterocyclic radicals and fused ring structures formed therefrom containing from two to ten rings.

4. The method of claim 3, wherein Ar is selected from the group consisting of substituted or unsubstituted $C_6$–$C_{15}$ aryl radicals, substituted or unsubstituted $C_7$–$C_{13}$ aralkyl radicals, substituted or unsubstituted 3–6 member heterocyclic radicals, or a two or three ring fused ring structure thereof.

5. The method of claim 4, wherein Ar is a phenyl group.

6. The method of claim 5, wherein Ar is a phenyl group substituted with one or two moieties selected from the group consisting of straight-chained and branched, substituted and unsubstituted $C_1$–$C_{20}$ alkyl, aryl, aralkyl, amido, alkoxyl, secondary amino and tertiary amino groups.

7. The method of claim 6, wherein said phenyl group is substituted with one or two aralkyl, aryl, alkyl or tertiary amino groups.

8. The method of claim 5, wherein Ar is an unsubstituted phenyl group.

9. The method of claim 8, wherein said aromatic aminothiol is an ortho-aminothiophenol.

10. The method of claim 8, wherein said aromatic aminothiol is a meta-aminothiophenol.

11. The method of claim 8, wherein said aromatic aminothiol is a para-aminothiophenol.

12. The method of claim 1, wherein said aromatic aminothiol has the structure:

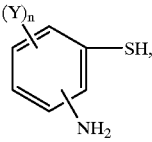

wherein Y is selected from the group consisting of straight-chained and branched, substituted and unsubstituted $C_1$–$C_{20}$ alkyl, aryl, aralkyl, amido, alkoxyl, secondary amino and tertiary amino groups; and n is between 0 and 4, inclusive.

13. The method of claim 12, wherein n is 0.

14. The method of claim 13, wherein the $NH_2$ group is meta to the SH group.

* * * * *